United States Patent [19]
Minka

[11] 3,949,769
[45] Apr. 13, 1976

[54] DENTAL FLOSS HOLDER

[76] Inventor: Karlis Minka, 204 E. Joppa Road, Towson, Md. 21204

[22] Filed: Jan. 28, 1975

[21] Appl. No.: 544,747

Related U.S. Application Data

[63] Continuation-in-part of Ser. No. 413,693, Nov. 7, 1973, abandoned.

[52] U.S. Cl. .................................................. 132/91
[51] Int. Cl.² .......................................... A61C 15/00
[58] Field of Search ........................... 132/89, 91, 92

[56] References Cited
UNITED STATES PATENTS

| | | | |
|---|---|---|---|
| 1,239,633 | 9/1917 | Shekler | 132/92 R |
| 2,217,917 | 10/1940 | Munro | 132/92 R |
| 2,870,773 | 1/1959 | Parks | 132/92 R |
| 3,759,272 | 9/1973 | Vincenti | 132/92 R |

*Primary Examiner*—G. E. McNeil

[57] ABSTRACT

A dental floss holder which includes a hollow handle adapted to receive a supply of dental floss, a cap assembled with the handle and provided with studs for supporting a length of floss which is pulled from the supply, the assembled cap and handle forming a clamping engagement and a groove for locking the floss so that is is held taut between the studs during flossing.

20 Claims, 4 Drawing Figures

DENTAL FLOSS HOLDER

CROSS-REFERENCE TO A RELATED APPLICATION

The present application is a Continuation-in-Part of application Ser. No. 413,693, filed Nov. 7, 1973 now abandoned.

SUMMARY OF THE INVENTION

A number of dental floss holders of a type disclosed herein have been proposed, however, none of them apparently are enjoying commercial success. The main difficulty is to obtain and maintain a taut floss between the supporting means by positively locking the end of the floss while satisfying the requirements of hygiene, convenience and simplicity. The difficulty is considerably more aggravated in case the floss is waxed and therefore slippery. The chief object of this invention is to overcome this difficulty by utilizing a principle based on a long wedging type frictional engagement of the end of the floss in an annular outwardly facing V-shaped groove formed between the cap and the handle. The floss is embedded in the V-shaped groove for almost the entire length thereof, and it is wedged and locked in the groove by a pulling force which is exerted on the floss during use. Due to the annular inward wedging and the long engagement of the floss in the groove, the locking force is proportional to the pulling force and it is found that there is practically no slippage irrespective of the type (waxed or unwaxed) or thickness of the floss. To achieve this result, the width of the V-shaped groove is of very small dimensions commensurate with the relatively small thickness of the floss. Nevertheless, because of the construction, the groove may be easily cleaned and the entrapment of unsanitary matter prevented. Other features of the invention also prevent the entrapment of unsanitary matter and provide for easy cleanability as it will be apparent hereinafter.

The supply of floss is placed in the hollow handle with one end of the floss remaining outside the threaded end of the handle and the cap is screwed on requiring no threading of the floss through holes or similar actions. The holder is convenient to operate because only a few simple motions are involved to put it in operating order, such as tightening of the cap on the handle, placing the floss on the supporting means of the studs and wedging it in the V-shaped groove, which are aided by additional features of the invention. The used floss is released completely by a short twist of the cap.

The holder is comprised essentially of only two relatively simple parts. The means for supporting the floss on the studs provide an easily cleanable structure which keeps the floss securely in place.

Other objects and features of the invention will be apparent from the following description and claims, and from the accompanying drawing.

DESCRIPTION OF THE PREFERRED EMBODIMENTS

Figure 1:
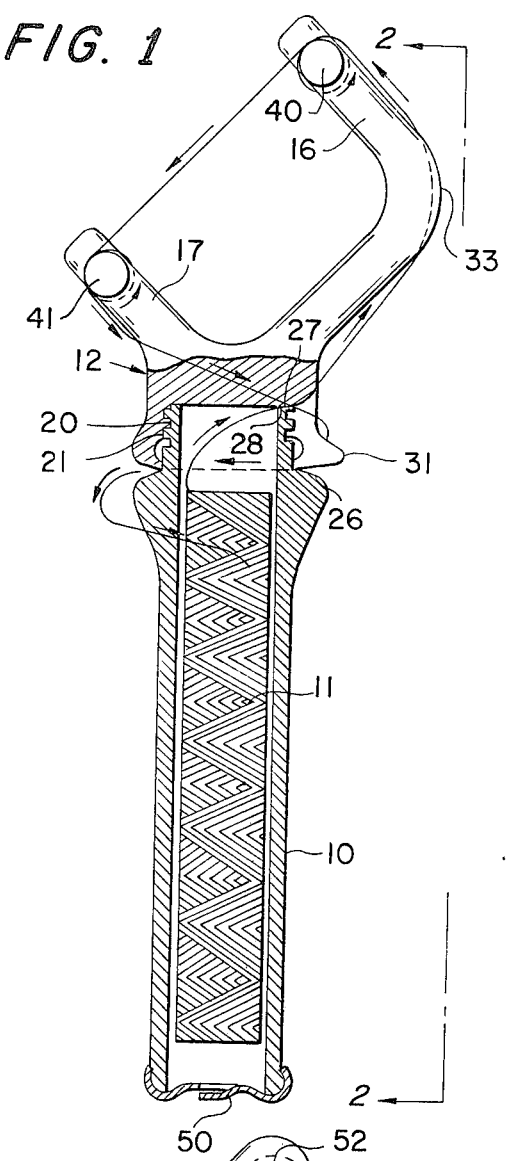
FIG. 1 is a partial sectional view of the holder showing the cap and handle assembly with a supply of floss inside the handle.

In FIG. 1, the hollow handle 10 is shown with a supply of floss 11. The cap 12, shown assembled with the handle, has a shank 15 and spaced apart studs 16 and 17 integral with the cap. The shank is hollow and has an inner wall provided with internal threads 20 for assembly with an externally threaded engaging end 21 of the handle. When the cap and the handle are screwed together, a cooperating rim 25 of the cap forms an annular outwardly facing V-shaped groove with a shoulder 26 on the handle and a bottom wall 27 of the cap engages an end wall 28 of the handle. The shoulder 26 is spaced longitudinally from the end wall 28 and extends transversely outwardly with respect to the longitudinal axis of the handle. In the preferred embodiment, the internal shank length extending from the bottom wall 27 to the inward portion of the rim 25 is slightly longer than the handle part extending from the end wall 28 to the inward portion of the shoulder 26, the rim 25, forming one side of the V-shaped groove being resilient to ensure the clamping and the wedging functions of the device. The resiliency is achieved preferably by providing the interior part of the rim with an internal annular groove 29 as shown in FIG. 1. It is also possible to make the shoulder 26 to be the resilient and/or a movable element with respect to the handle to ensure the proper functioning of the device. Also, the rim does not have to engage the shoulder when the cap and the handle are screwed together with the beginning of the floss clamped between the bottom wall 27 and the end wall 28, provided that the width of the formed V-shaped groove is of sufficient dimensions to allow the wedging of the floss in the groove. The term "resilient" as used herein defines a property of the element described by the term as being substantially more resilient in the direction of the longitudinal axis of the assembled holder than the rest of the part of which the element is a constituent.

Figure 2:
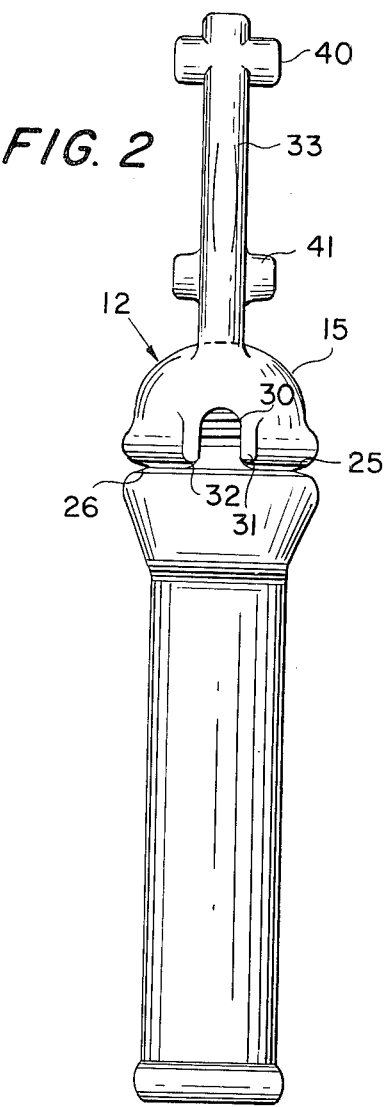
FIG. 2 is a view of the holder looking along 2—2 of FIG. 1.

The studs 16 and 17 are of a suitable size and suitably spread apart to fit conveniently inside a person's mouth and are provided with means for supporting a portion of the floss that is used for flossing the teeth. A length of floss is pulled out of the handle through a passageway, preferably a slot 30, when the cap is partly unscrewed from the handle, the slot being cut out in the shank in line with stud 16 and provided with lips 31 and 32 as best seen in FIG. 2. The cap is then screwed down tight on the handle to clamp the beginning of the length of floss between the bottom wall 27 and the end wall 28 at the point where the floss exits through the slot 30, and to form the V-shaped groove. The floss is then threaded up the outside of stud 16 in a suitable rounded groove 33 and wrapped diagonally around the structure formed by a cross arm 40 and the top part of stud 16 so that it may not be easily dislodged from its support. It is then stretched taut across to stud 17 and wrapped around a cross arm 41 and the top part of stud 17 in the same manner as on stud 16. The end of the floss is then pulled across to the opposite side of the cap, guided between the lips 31 and 32 and then wedged in the V-shaped groove.

The floss is shown diagrammatically in the drawing in order not to obscure the features of the invention and the arrows indicate the threading direction of the floss. The terms "cross arm" and "cross arm and the top part of stud" as used herein are not limited to the illustrations in the drawing, as obvious variations may be employed.

After use, the cap is unscrewed partly whereby the floss is released from engagement between the bottom wall 27 and the end wall 28 which constitute the clamping means, and between the elements 25 and 26 of the cap and handle. After the floss has been removed from studs 17 and 16, a new length of floss may be pulled from the handle and the used floss may be cut off by a cutter 50 located on the bottom end of the handle. The cap and handle may be disassembled, rinsed and assembled together again. It will be noted that in the process of placing a new length of floss in position, the beginning of the length of floss to be used is clamped first and then the floss after being stretched between the studs is wedged in the V-shaped groove. By this method the tautness of the floss may be easily controlled. This would be difficult to achieve, if both ends of the floss would be locked simultaneously.

The end of the floss may be made to enter the V-shaped groove without the guidance provided by the lips 31 and 32 which may be eliminated if desired, however, they are preferred because of a better control of the floss afforded thereby. The threads 20 of the shank and the threads of the threaded engaging end 21 of the handle are square threads, so that when the cap is screwed tightly onto the handle there is no expansion force on the wall forming the shank, such as would result if regular V-shaped threads were used. Because of the slot 30, the expansion force resulting from the V-shaped threads could break the cup. Instead of square threads, another type of threads generally known in machine design as buttress threads may be used to accomplish the same result. Other types of passageways such as a hole may be used in place of the slot 30, but a hole would require a more difficult threading operation to initially load the holder.

Figure 3:
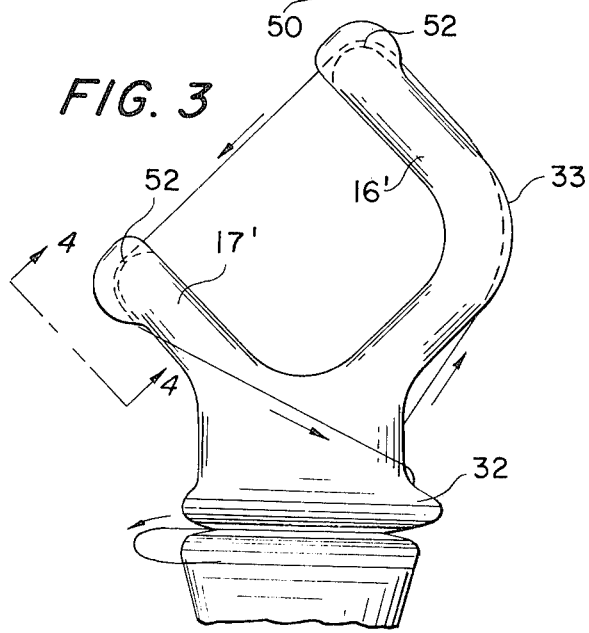
FIG. 3 is a partial view of the holder showing an alternate cap.
Figure 4:
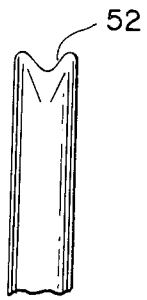
FIG. 4 is a view looking along 4—4 of FIG. 3.

Alternate forms of studs, such as the grooved studs 16' and 17' shown in FIGS. 3 and 4, may be used. On these studs, the means for supporting the floss comprises supporting grooves 52 at the top ends of the studs. The supporting grooves extend to the outer sides of the studs enabling to make the grooves shallow, thus preventing the entrapment of unsanitary matter and providing easy cleanability while making it extremely difficult to dislodge the floss during use.

Both types of studs are located preferably in such a position with respect to the handle 10 whereby the longitudinal axis of the handle intersects approximately the middle of the floss between the studs to minimize any possible torque on the screwed on cap due to manipulation of the holder during use.

The disposition of the elements to carry out the invention is not necessarily restricted to the arrangement illustrated in the drawing as such variations may be made that fall within the scope of the invention as claimed. For example, the outer wall of the shank may have external threads cooperating with an internally threaded engaging end of the handle. The bottom wall may be located at the end of an externally threaded shank, engaging an end wall spaced longitudinally inside the handle which has an internally threaded engaging end. Also, the V-shaped groove may be a direct outward extension of the engagement between the bottom wall and the end wall, adjoining the bottom wall and the end wall, and in combination with an externally or internally threaded shank and a cooperating threaded engaging end of the handle.

Although the invention has been described above in a preferred embodiment and in a number of modifications, it will be understood by those skilled in the art that other modifications may be made within the spirit of the invention. It is intended that no limitations be placed on the invention exept as defined by the scope of the appended claims.

I claim:

1. A dental floss holder comprising:
   a. a hollow handle adapted to receive a supply of floss and having a longitudinal axis, said handle having an engaging end,
   b. a cap having a shank adapted for assembly with said engaging end of the handle,
   c. said engaging end having first clamping means and a shoulder extending transversely outwardly with respect to said axis,
   d. said cap having second clamping means for cooperating with said first clamping means to clamp the beginning of a length of floss therebetween and a cooperating rim extending transversely outwardly with respect to said axis for forming an annular outwardly facing V-shaped groove with said shoulder on the handle upon assembly with said engaging end thereof,
   e. the width of said V-shaped groove being of dimensions sufficient for wedging of the end of said length of floss in said V-shaped groove,
   f. spaced apart studs on said cap, the studs having means for supporting a portion of said length of floss therebetween, and
   g. a passageway to permit said length of floss to pass from the inside of the handle to the outside of the holder.

2. A holder as in claim 1, wherein said first clamping means comprises an end wall and said second clamping means comprises a bottom wall.

3. A holder as in claim 1, wherein the outer wall of said shank is adapted for assembly with said cooperating engaging end of the handle.

4. A holder as in claim 1, wherein said means for supporting a portion of a length of floss comprises a cross arm and the top part of one of said studs for wrapping the floss thereon.

5. A holder as in claim 1, wherein said means for supporting a portion of a length of floss comprises a supporting groove on the top end of one of said studs for placing the floss thereon.

6. A holder as in claim 1, wherein said handle has a cutter on the bottom end thereof for cutting off used floss.

7. A holder as in claim 1, wherein said holder is provided with said supply of floss.

8. A holder as in claim 1, wherein the outside diameter of said rim is larger than the outside diameter of said shoulder.

9. A holder as in claim 2, wherein said shoulder on the handle is spaced longitudinally from said end wall.

10. A holder as in claim 2, wherein said outwardly extending shoulder adjoins said end wall and said rim adjoins said bottom wall.

11. A holder as in claim 9, wherein said shoulder forming one side of the V-shaped groove is resilient.

12. A holder as in claim 9, wherein said rim forming one side of the V-shaped groove is resilient.

13. A holder as in claim 9, wherein said shank is hollow and has an inner wall adapted for assembly with said cooperating engaging end of the handle, and said shank has a slot therein to provide said passageway.

14. A holder as in claim 13, wherein said slot has an outwardly extending lip at least on one side thereof for guiding said end of the length of floss.

15. A holder as in claim 13, wherein said inner wall has square threads for assembly with said engaging end of the handle.

16. A holder as in claim 12, wherein resiliency of said rim is provided by an internal annular groove.

17. A holder as in claim 13, wherein said engaging end has square threads for assembly with said shank.

18. A holder as in claim 3, wherein said shank is provided with said passageway.

19. A holder as in claim 3, wherein said handle is provided with said passageway.

20. A holder as in claim 5, wherein said supporting groove extends to the outer side of said one stud for placing the floss thereon.

* * * * *

UNITED STATES PATENT AND TRADEMARK OFFICE
CERTIFICATE OF CORRECTION

PATENT NO. : 3949769
DATED : Apr. 13, 1976
INVENTOR(S) : Karlis Minka

It is certified that error appears in the above-identified patent and that said Letters Patent are hereby corrected as shown below:

In the drawing, FIG. 1, the upper part of the partial sectional view should appear as follows:

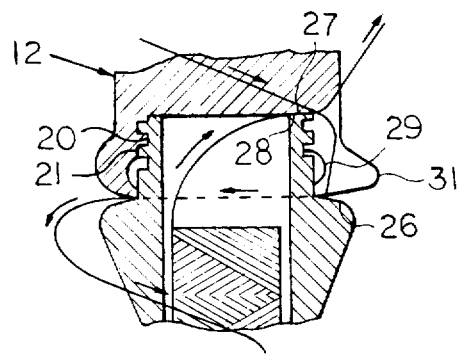

Signed and Sealed this

Nineteenth Day of October 1976

[SEAL]

Attest:

RUTH C. MASON
Attesting Officer

C. MARSHALL DANN
Commissioner of Patents and Trademarks